United States Patent [19]

Heydenreich et al.

[11] 4,369,293

[45] Jan. 18, 1983

[54] CATALYST FOR THE PREPARATION OF BISPHENOLS

[75] Inventors: Frieder Heydenreich, Ratingen; Claus Wulff, Krefeld; Lothar Klein, Leverkusen; Hans-Jürgen Meissner; Norbert Bachem, both of Krefeld, all of Fed. Rep. of Germany

[73] Assignee: Bayer Aktiengesellschaft, Leverkusen, Fed. Rep. of Germany

[21] Appl. No.: 273,005

[22] Filed: Jun. 12, 1981

Related U.S. Application Data

[63] Continuation-in-part of Ser. No. 172,936, Jul. 28, 1980, abandoned.

[30] Foreign Application Priority Data

Jul. 31, 1979 [DE] Fed. Rep. of Germany ....... 2931036

[51] Int. Cl.³ .............................................. C08F 8/34

[52] U.S. Cl. ................................ 525/333.5; 525/350; 568/727

[58] Field of Search ............... 525/332, 350, 344, 379, 525/333.5

[56] References Cited

U.S. PATENT DOCUMENTS 2,520,917 9/1950 Dickey .............................. 525/344

*Primary Examiner*—C. A. Henderson
*Attorney, Agent, or Firm*—Connolly and Hutz

[57] ABSTRACT

A catalyst for the preparation of bisphenols from phenols and compounds containing carbonyl groups consisting of a styrene/divinyl benzene copolymer into which are introduced sulphochloride groups which, in turn, have been partly reacted with mercaptoalkylamine and partly hydrolyzed to form sulphonic acid groups.

1 Claim, No Drawings

CATALYST FOR THE PREPARATION OF BISPHENOLS

CROSS REFERENCE TO RELATED APPLICATION

This application is a continuation-in-part of application Ser. No. 172,936 filed July 28, 1980 and now abandoned.

Ion exchangers are used as catalysts in the commercial preparation of bisphenols from phenols and compounds containing carbonyl groups. The activity thereof may be increased by co-catalysts. These co-catalysts are generally mercapto-compounds some of which are ionically bound to the ion exchanger. For example, mercaptopropionic acid (U.S. Pat. No. 2,468,982), phenol-soluble mercaptans (British Pat. No. 1,185,102) and thiazolidine (German Auslegeschrift No. 2,164,339) have been used as co-catalysts.

These co-catalysts are generally not bound or are only ionically bound to the ion exchanger and are therefore soluble in the reaction medium. They pass at least partly into the reaction product during working-up and adversely affect the quality thereof.

The present invention is based on the observation that co-catalysts may be bound to the ion exchanger skeleton by covalent bonds without loss of activity. Accordingly, the co-catalysts are insoluble and no longer enter the reaction product.

Accordingly, the present invention relates to a catalyst for the preparation of bisphenols from phenols and compounds containing carbonyl groups, comprising a styrene/divinyl benzene copolymer into which are introduced sulphochloride groups which in turn have been partly reacted with a mercaptoalkylamine and partly hydrolysed to form sulphonic acid groups. Generally, the catalyst may be prepared as follows:

A preferably swollen styrene/divinyl benzene copolymer is reacted to form a sulphochloride by the processes normally used for the preparation of aromatic sulphochlorides. The known swelling agents, for example 1,2-dichloroethane, may be used as the swelling agent. The degree of substitution should generally amount to $\geq 0.9$. Chlorosulphonic acid is preferably used for preparing the sulphochloride.

On completion of chlorosulphonation, the excess chlorosulphonic acid is separated off and approximately 15 to 40 mole percent of the sulphochloride groups are reacted with the mercaptoamine to form the sulphonamide. The residual sulphochloride groups are then hydrolysed, preferably by distillation with steam, to form sulphonic acid groups and any residues of swelling agent or solvent still present are removed. The water-moist catalyst may be dried thermally or, preferably, by dehydration with a phenol.

Styrene/divinyl benzene copolymers suitable for the preparation of the catalyst are known products having a divinyl benzene content of from 0.2 to 25% being preferred.

In the context of the present invention, mercaptoalkylamines are compounds which simultaneously contain one or more primary or secondary amino groups and at least one mercapto group. In principle, mercaptoarylamines may also be used for the preparation of the catalysts, although mercaptoalkylamines are preferred. Particularly suitable mercaptoalkylamines are, for example, 2-mercaptoethylamine, 2-mercaptoisopropylamine, 3-mercaptobutylamine and mercaptopentylamine.

To prepare the catalyst one can also start from sulfonated ion exchanger resins, operating as follows:

The desiccated sulfonic acid groups containing ion exchanger resin is poured into 1.2-dichloro ethane, serving as a swelling and stirring medium. Under boiling at reflux thionyl chloride is added and the hydrochloric acid obtained as well as the sulfur dioxide formed derived from the mixture. A satisfactory reaction is achieved only when catalytic amounts of pyridine are added. Upon termination of the reaction with thionyl chloride the excess thionyl chloride is removed, followed by the reaction with mercapto amine as well as the terminating hydrolysis. After desiccation which can be made thermally or preferably by dehydration with phenol, a catalyst of high activity is obtained. Even after 50 days' storage no decrease in activity is observed. No sulfur can be proven in the mother liquors, i.e., the catalyst shows no tendency to bleeding.

Suitable starting materials for preparing this catalyst are sulfonic acid containing ion exchanger resins having a matrix from styrene and divinyl benzene; the content of divinyl benzene can amount to 0.2–25%. The degree of sulfonation of the resin is not decisive, however, resins with an utmost complete sulfonation are preferably used.

The catalysts according to the present invention may be used for the preparation of bisphenols. Phenols suitable for use as starting materials for this purpose are, in particular, phenol and 2,6-dimethyl phenol, whilst compounds containing carbonyl groups suitable for use as starting materials are, in particular, acetone and formaldehyde.

In general, from 85 to 99.8 parts, by weight, of the phenol are reacted with from 0.2 to 15 parts, by weight, of the compound containing carbonyl groups at temperatures of from 45° to 130° C., optionally in the presence of a solvent, in a fixed or fluidised catalyst bed.

EXAMPLE 1

1700 g of a polystyrene cross-linked with 2% of divinyl benzene and having a residual moisture content of 0.1% ($H_2O$) are suspended, with stirring, in 5 liters of dry 1,2-dichloroethane. 2 liters of chlorosulphonic acid are added at from 0° to 5° C. On completion of chlorosulphonation, 100 g of cysteamine-hydrochloride are added, with stirring, at room temperature. On completion of the reaction, the product is steam distilled, the chlorosulphonic acid groups being hydrolysed. The thus-prepared modified catalyst has an H-equivalent of 3.65.

For comparison, the test is repeated without addition of the cysteamine-hydrochloride. The H-equivalent of the thus-obtained product is 4.95.

The modified catalyst (A) according to the present invention and the comparison product (B) reacted with β-mercaptopropionic acid as co-catalyst have phenol and acetone added. The results of the two tests are shown in the following Table:

|  | A | B |
|---|---|---|
| Quantities used |  |  |
| Phenol | 282.0 g | 282.0 g |
| Acetone | 14.5 g | 14.5 g |
| β-mercaptopropionic acid | — | 0.12 g |
| Ion exchanger resin | 37.5 g | 37.5 g |

| -continued | A | B |
|---|---|---|
| Acetone conversion after: | | |
| 1 hour | 77.1 | 52.6 |
| 2 hours | 87.3 | 66.0 |
| 3 hours | 94.5 | 76.3 |
| 4 hours | 96.9 | 81.8 |
| 7 hours | 98.4 | 91.4 |
| Colour of the mother liquor | light | dark |

EXAMPLE 2

14 g of a dry, sulfonic acid groups containing resin from styrene and 2% divinyl benzene (total capacity 4.2 mval/l) are applied in 100 ml of 1.2-dichloro ethane. Under exclusion of moisture, slight stirring and boiling at reflux, 12 g of thionyl chloride are slowly added dropwise. Before adding thionyl chloride 0.4 ml pyridine were added to the mixture. On termination of the dropwise addition, stirring is continued for further 2 hours. The excess of thionyl chloride and 1.2-dichloro ethane is sucked off from the mixture by means of a frit or by distillation-optionally, under vacuum. Thereafter, washing with 1.2-dichloro ethane takes place several times to remove remainders of $SOCl_2$.

Subsequently, the mixture is again poured into 1.2-dichloro ethane and 0.8 g cysteamine hydrochloride added under stirring at room temperature. After the reaction is terminated, the mixture is subjected to a water vapour distillation whereby the sulfochloride groups are hydrolyzed. The H-equivalent of the thus prepared catalyst amounts to 3.7.

In a comparison test the modified catalyst (A) according to the present invention is compared with a non-modified catalyst, to which $\beta$-mercapto propionic acid was added as a co-catalyst.

| Amounts applied | A (in g) | B (in g) |
|---|---|---|
| phenol | 1128 | 1128 |
| acetone | 58 | 58 |
| $\beta$-mercaptopriopionic acid | — | 0.48 |
| catalyst | 150 | 150 |
| Reaction temperature: 65° C. | | |
| acetone conversion after 4 hrs: | 97.5% | 81.0% |
| Coloration of the mother liquor | light | dark |

We claim:

1. A catalyst suitable for preparing bisphenols from phenols and compounds containing carbonyl groups comprising a styrene/divinyl benzene copolymer containing from 0.2 to 25% by weight of polymerized divinyl benzene and having a degree of substitution of at least 0.9 groups derived from sulphochloride groups of which 15 to 40 mole percent are sulfonic acid mercapto alkyl amide groups and the remainder are sulfonic acid groups.

* * * * *